United States Patent [19]
Zaleski

[11] Patent Number: 5,643,276
[45] Date of Patent: Jul. 1, 1997

[54] APPARATUS AND METHOD FOR PROVIDING DESIRED ROTATIONAL ORIENTATION TO AN INTRAOCULAR LENS

[75] Inventor: Edward R. Zaleski, Santa Ana, Calif.

[73] Assignee: Allergan, Waco, Tex.

[21] Appl. No.: 540,428

[22] Filed: Oct. 10, 1995

[51] Int. Cl.⁶ ........................................ A61F 9/00
[52] U.S. Cl. ........................................ 606/107
[58] Field of Search ................. 606/107, 1, 166, 606/170; 623/6, 1

[56] References Cited

U.S. PATENT DOCUMENTS

| | | | |
|---|---|---|---|
| 4,210,146 | 7/1980 | Banko | 606/171 |
| 4,681,102 | 7/1987 | Bartell. | |
| 4,747,404 | 5/1988 | Jampel et al.. | |
| 4,785,810 | 11/1988 | Baccala et al.. | |
| 4,834,094 | 5/1989 | Patton et al.. | |
| 4,836,201 | 6/1989 | Patton et al.. | |
| 4,844,065 | 7/1989 | Faulkner. | |
| 4,934,363 | 6/1990 | Smith et al. | 606/107 |
| 4,976,716 | 12/1990 | Cumming. | |
| 5,098,439 | 3/1992 | Hill et al.. | |
| 5,275,604 | 1/1994 | Rheinish et al. | 606/107 |
| 5,476,513 | 12/1995 | Brady et al. | 623/6 |
| 5,494,484 | 2/1996 | Feingold | 606/107 |
| 5,496,328 | 3/1996 | Nakajima et al. | 606/107 |

FOREIGN PATENT DOCUMENTS

| | | | |
|---|---|---|---|
| 405103809 | 4/1993 | Japan | 606/107 |
| 2191439 | 12/1987 | United Kingdom. | |
| 9407436 | 4/1994 | WIPO. | |
| 9420027 | 9/1994 | WIPO. | |
| 9628121 | 8/1996 | WIPO. | |

Primary Examiner—Sam Rimell
Assistant Examiner—Justine Yu
Attorney, Agent, or Firm—Frank J. Uxa

[57] ABSTRACT

Apparatus for inserting intraocular lenses (IOLs) into eyes are disclosed. The apparatus comprises an insertion tube, and an injector rod having a distal tip capable of engaging an intraocular lens. A rotating assembly is provided to controllably rotate the rod as it moves distally through the insertion tube. The rotation of the injector rod is imparted to the IOL in such a manner that the IOL is also rotated as it moves through the insertion tube. The degree of rotation of the IOL is controlled to place the IOL in an orientation for final implantation in the eye with reduced risk of damaging the eye. Methods for inserting an IOL into an eye using such apparatus are also disclosed and are within the scope of the present invention.

19 Claims, 3 Drawing Sheets

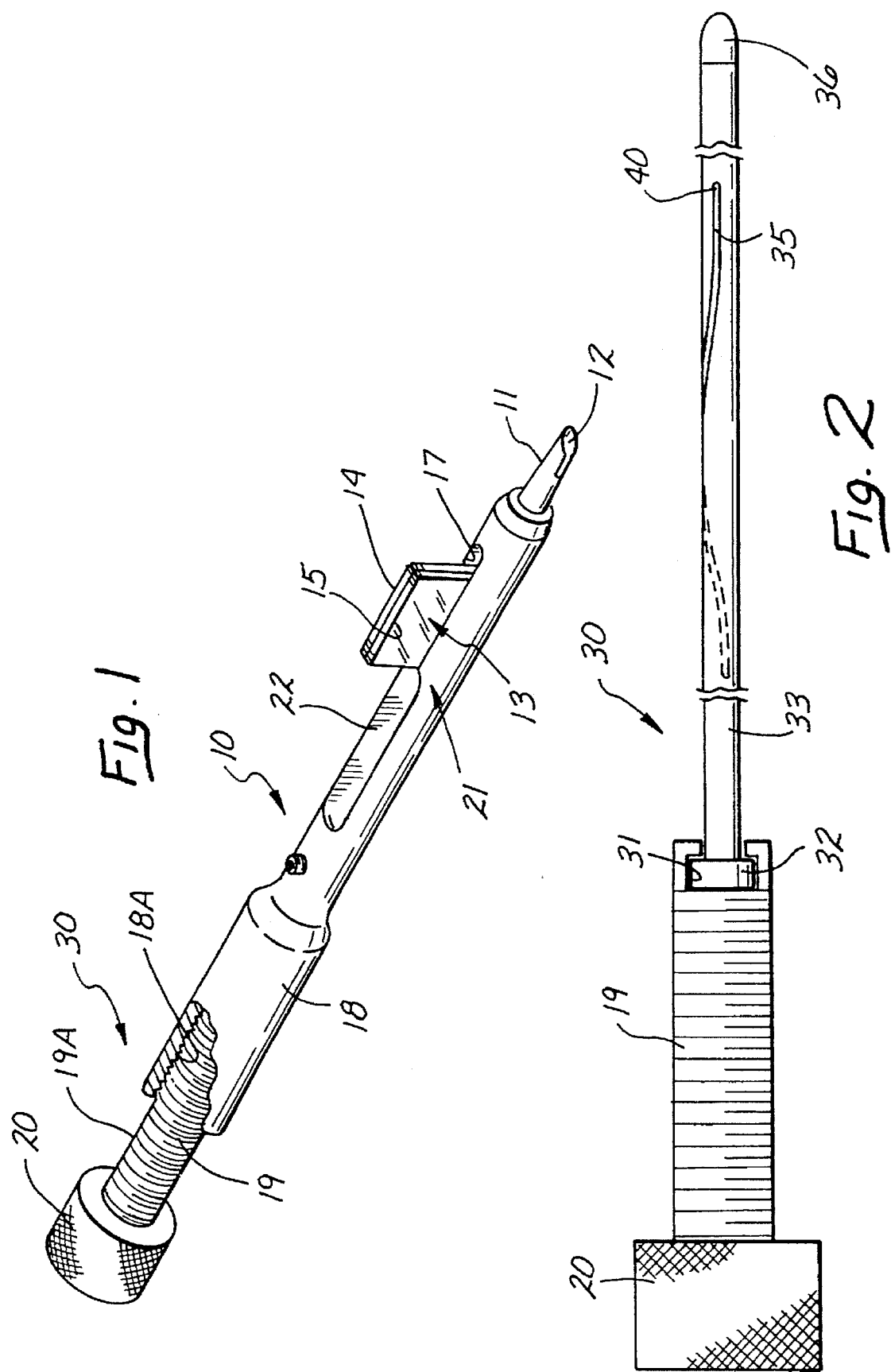

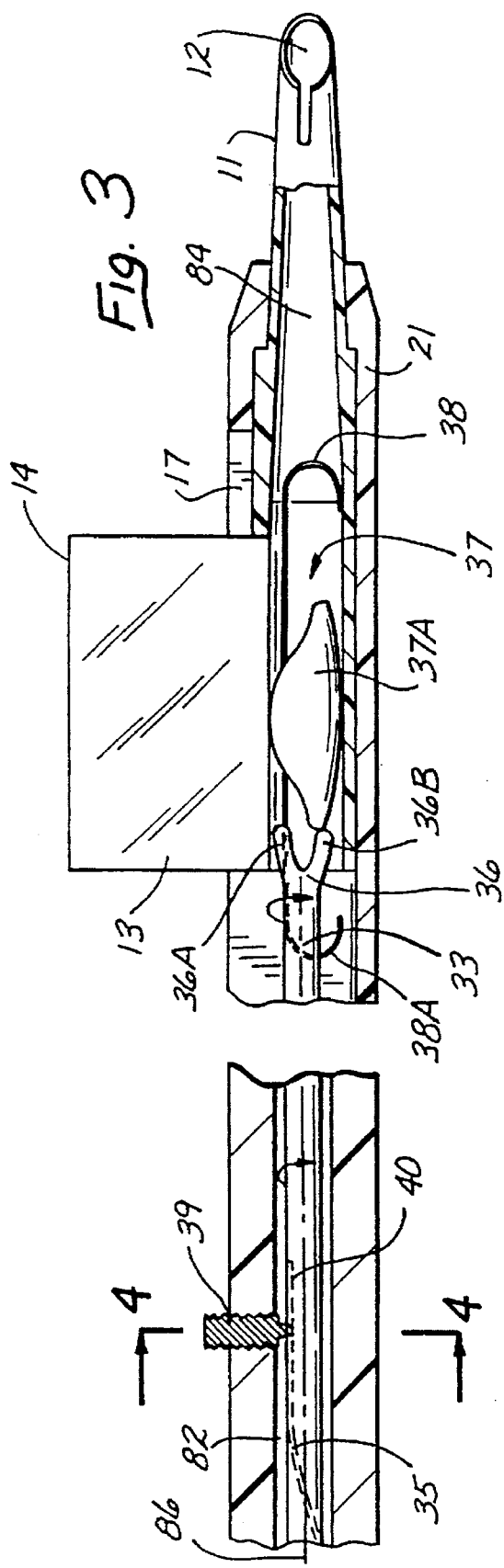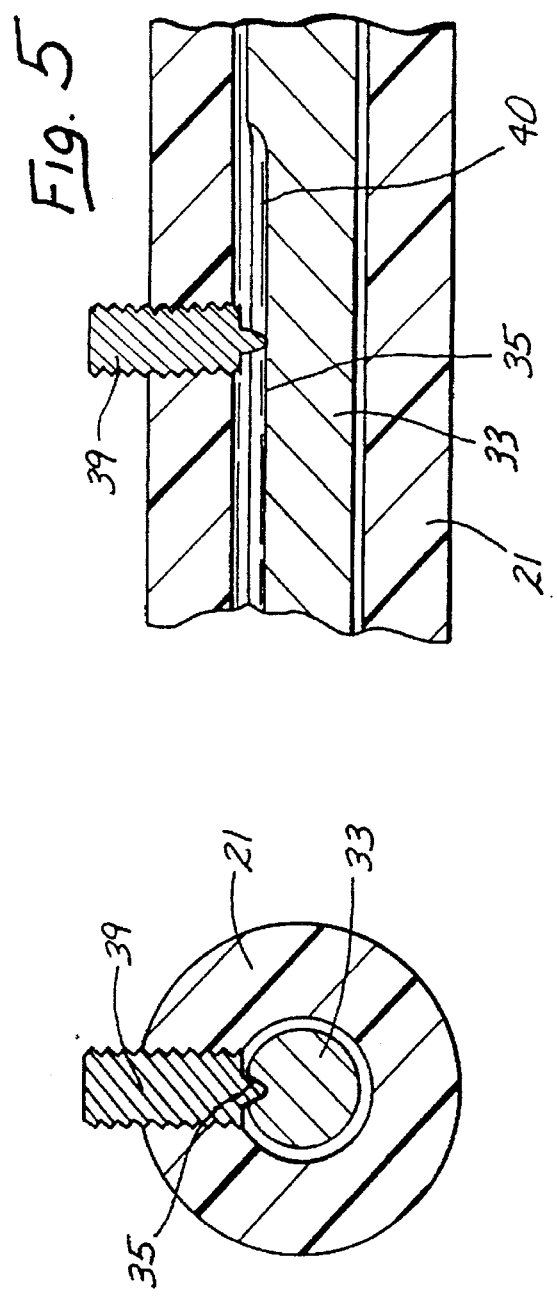

APPARATUS AND METHOD FOR PROVIDING DESIRED ROTATIONAL ORIENTATION TO AN INTRAOCULAR LENS

BACKGROUND OF THE INVENTION

The present invention relates to apparatus and methods for inserting an intraocular lens through a small incision into an eye. More particularly, the invention relates to such apparatus and methods wherein the desired rotational orientation of the lens as it is inserted in the eye is easily, controllably and effectively achieved.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic, which extends from the optic and becomes affixed in the eye to secure the lens in position. The optic normally includes an optically clear lens. Implantation of such IOLs into the eye involves making an incision in the eye. Making the incision as small as possible reduces trauma and speeds healing.

IOLs are known which are foldable (deformable) so that the IOL can be inserted into the eye through an incision smaller than the diameter of the lens and subsequently permitted to unfold after it has passed through the incision. A substantial number of instruments have been devised to aid in inserting such a foldable lens into the eye. The advantages of the foldable lens in cataract removal and lens replacement are so significant that many of the lens replacement procedures are performed with folded lenses inserted into the eye, and released therein to assume their initial unfolded state.

The success of foldable IOLs is enhanced by the surgeon's ability to control the orientation of the IOL during lens insertion. An IOL which is not correctly oriented as it is released from the inserter apparatus into the eye may require relatively difficult reorientation and/or can damage one or more parts of the eye. The risk of eye damage is particularly apparent in situations where the leading or superior fixation member or haptic, for example, comprising an elongated filament, is not properly oriented as it exits the insertion apparatus.

Some of the most generally accepted insertion apparatus employ a hollow insertion tube having a diameter which permits the folded IOL to pass freely through the tube without permanent deformation, and without causing the surgeon to apply excessive force to overcome friction between the walls of the insertion tube and the IOL. Excessive force can result in the premature ejection of the IOL before the surgeon is ready to position it within the patient's eye.

Unfortunately, the folded IOL tends to rotate axially within the insertion tube in an unpredictable manner as the IOL is moved distally through the tube prior to ejection. This means that the surgeon does not know what the orientation of the IOL will be upon its release from the insertion tube. As explained above, it is advisable for the surgeon to have control of the orientation of the IOL as it exits the insertion tube. Despite the many modifications of IOL injection devices, more precise control of the rotation of the IOL within the insertion tube and of the orientation of the IOL as it is ejected from the insertion tube remains a continuing goal.

It would be advantageous to provide IOL insertion apparatus and methods which facilitate the passage of a folded IOL through the apparatus in a controlled manner to achieve the desired orientation as the IOL is released into the eye.

It would be further advantageous to provide IOL insertion apparatus and methods which control the extent of rotation of the folded IOL during the insertion so that the surgeon knows or can predict the positioning of the IOL within the eye and/or reduce the risk of damaging the eye as the IOL is released into the eye.

SUMMARY OF THE INVENTION

New apparatus for inserting IOLs and methods for using such apparatus have been discovered. The present apparatus enable the surgeon to achieve a desired degree of orientation, for example, rotational orientation of the IOL as the lens is released from the insertion apparatus, thus providing for the use of effective, reliable, and non-excessive amounts of force to insert a folded IOL into an eye. In addition, the present system reduces the need for additional manipulation of the IOL by the surgeon to achieve the desired placement of the IOL within the eye. The present invention is straightforward, easy to practice, and involves little or no modification of surgical techniques. In other words, surgeons need not learn a different surgical procedure for inserting an IOL into the eye, nor does the IOL need to be modified to accommodate the present apparatus and methods.

In one broad aspect, the present invention comprises apparatus for inserting IOLs into an eye which include an insertion tube defining a hollow passage, for example, through at least a portion of which a folded intraocular lens can be moved. This tube has an ejection port, preferably at its distal tip, from which the lens is passed for insertion into an eye. An injector rod is also included and is longitudinally movable within the hollow space of the tube. The distal portion of the rod is adapted to contact the folded IOL within the passage of the tube to urge the folded IOL distally through the passage. A rotation assembly is operatively associated with the injector rod so that the rod is rotated about its longitudinally axis a controlled amount as the rod is moved distally through the insertion tube. The controlled rotation of the injector rod imparts a degree of rotation to the folded IOL as it moves distally through the hollow space of the insertion tube. Rotating the IOL as it moves distally through the hollow space of the insertion tube provides for the IOL, and in particular the leading or superior fixation member of the IOL, to be oriented during the IOL insertion process so as to reduce, or even eliminate, the risk of eye damage as the IOL is being inserted into the eye. In addition, the orientation of the IOL as it exits the insertion tube is predictable and controlled, thereby making the entire insertion process easier and reducing the risk of surgical error. Also, the present system very effectively places the IOL in the desired location in the eye so that a reduced amount of repositioning of the IOL in the eye is needed.

In one embodiment, the rotation assembly comprises a cam race and a cam follower. A particularly useful embodiment provides for a rotation assembly in which a cam race is disposed on the injector rod and the cam follower is disposed on the insertion tube. Of course other constructions or configurations are effective to provide the desired controlled rotation and are included within the scope of the present invention. For example, the cam race can be disposed on the insertion tube and the cam follower can be disposed on the injector rod. Also, the rotation assembly can include a worm gear and a worm gear guide. Additionally, the wall of the insertion tube and the injector rod can be matingly configured, for example, threaded, to facilitate the desired, controlled degree of rotation. In fact, any suitable construction which provide for controlled rotation of the injector rod relative to the insertion tube as the rod is moved distally in the tube may be employed and is within the scope of the present invention.

In order to more effectively transmit the rotation of the injector rod to the IOL, it is preferred that the injector rod is structured to engage the folded IOL being moved distally through the insertion tube. Numerous constructions and configurations of such engaging structure may be employed and are included within the scope of the present invention. In one embodiment, the injector rod includes a forceps-like element adapted to engage the distally moving IOL. The forceps-like element (or other IOL engaging structure) should be sized so as to contact, preferably hold or grip, the IOL with sufficient positive force that the IOL rotates with the injector rod. On the other hand, the forceps-like element (or other IOL engaging structure) should allow the IOL to be released from the insertion apparatus, for example, into the eye, when desired. Although movable forceps may be used, the forceps-like element preferably includes at least two, and more preferably only two, spaced apart members, for example, fork members or arms, which are substantially stationary relative to each other.

Another aspect of the invention includes methods for inserting an intraocular lens into the eye. Such methods comprise:

placing an IOL in a folded condition in an insertion apparatus in accordance with the present invention;

positioning the ejector port of the apparatus in proximity to or through an incision in the eye; and moving the injector rod of the apparatus distally so that the IOL is inserted into the eye.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a side perspective view of an insertion apparatus in accordance with the present invention.

FIG. 2 is a side view, partly in cross-section, of the injector rod-plunger assembly removed from the body of the insertion apparatus shown in FIG. 1.

FIG. 3 is a side cross-sectional view of the insertion apparatus shown in FIG. 1 with the injector rod engaging the IOL to be inserted into an eye.

FIG. 4 is a cross-sectional view, taken generally along line 4—4 of FIG. 3.

FIG. 5 is an enlarged fragmentary side cross-sectional view of the cam follower engagement with the cam race shown in the left portion of FIG.3.

DETAILED DESCRIPTION OF THE PREFERRED EMBODIMENTS

Figure 6:
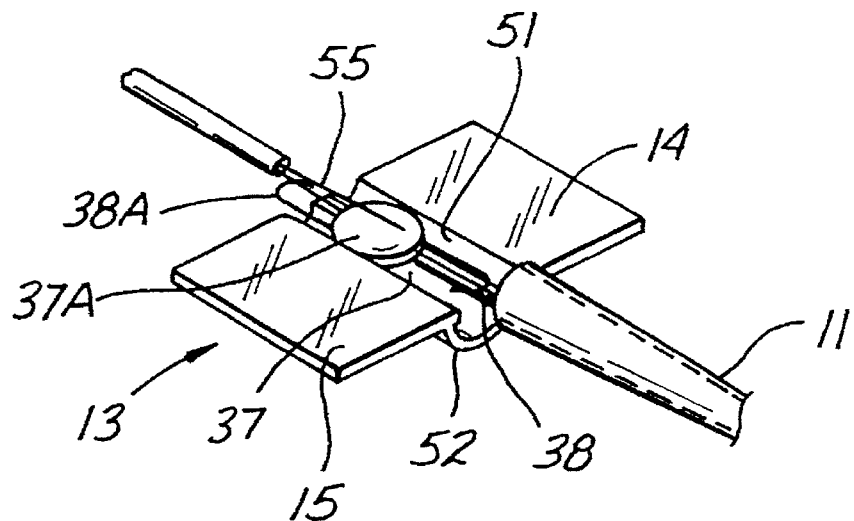
FIG. 6 is a perspective view of a folding device shown in the open position.

FIG. 1 illustrates an IOL insertion apparatus, shown generally as 10. The apparatus 10 comprises body 21, and a folding cartridge 13 including a forward tube 11 having an ejector port 12 at its distal end. The body 21 of injection apparatus 10 is an integrally formed unit. Folding cartridge 13 has folding leaves 14 and 15 which extend through opening 17 in the outer wall of the body 21. Proximal end portion 18 can be sized to completely and closely encompass plunger 19 of injector rod-plunger assembly 30, which has a plunger cap 20 affixed to its proximal end.

Proximal end portion 18 is hollow and includes a threaded surface 18A, the threads of which matingly engage the threads 19A on the outer surface of plunger 19.

Insertion apparatus 10 includes a slot 22 which extends from the proximal portion of opening 17 and connects therewith. Slot 22 is elongated in a direction parallel to the longitudinal axis of insertion apparatus 10. Slot 22 is sufficiently wide to permit the closed folding members 51 and 52, shown in FIG. 6, to fit therethrough, and sufficiently long to permit folding cartridge 13 to be inserted therein, so that the folding cartridge can be subsequently moved into connecting opening 17, which is sufficiently narrow to hold the folding cartridge in a fully closed position.

As shown in FIG. 3, the distal end portion of body 21 is hollow. When loading cartridge 13 is inserted into body 21, as shown in FIG. 3, the hollow space 82 defined by the body is aligned with the hollow space 84 defined by the loading cartridge 13. The combination of the joined body 21 and cartridge 13 can be considered a hollow tubular member defining a hollow space through which the injector rod 33 can pass longitudinally.

FIG. 2 shows injector rod-plunger assembly 30 with locking enclosure 31 holding injector rod cap 32. Injector rod 33 has disposed on its surface a cam race 35.

FIGS. 3, 4 and 5 show cam follower 39 engaging cam race 35. As injector rod 33 is moved distally toward ejection port 12, the cam follower 39 rotates the injector rod 33 in a clockwise direction, viewed from the proximal end of the apparatus. Cam race 35 includes a distal end portion 40 which is longitudinally positioned parallel to the longitudinal axis of the injector rod 33. This permits injector rod 33 to be advanced in contact with IOL 37 and to move IOL 37 beyond its initial position in folding cartridge 13 with no rotation. FIG. 5 is an enlarged side sectional view of a portion of the apparatus of FIG. 3 showing cam follower 39 disposed in the distal end portion 40 of the cam race 35. Once the curved portion of cam race 35 engages cam follower 39, injector rod 33 and IOL 37 begin to rotate.

With reference to FIGS. 2 and 3, the distal end region 36 of injector rod 33 is configured so as to come into contact with the folded optic 37A of IOL 37 and to cause the folded optic to rotate as the injector rod is rotated. Specifically, distal end region 36 includes fixed, spaced apart arms 36A and 36B which are positioned and sized to receive a portion of the folded optic 37A therebetween. Thus, as injector rod 33 is moved distally and rotated, so too is folded IOL 37 moved distally and rotated. As IOL 37 passes out of ejector port 12, it is removed from distal end region 36 of injector rod 33. However, because of the controlled rotation feature of insertion apparatus 10, the IOL 37 exits the ejector port 12 in a predictable planar orientation, making insertion of the IOL into the eye easier, more predictable, less dependent on surgical technique and less risky as it relates to possible eye damage.

FIG. 6 illustrates the manner in which lens cartridge 13 produces the desired result of folding IOL 37. Hinge folding leaves 14 and 15 are used to open and close folding members 51 and 52, respectively. IOL 37 (in an unfolded state) is placed on folding members 51 and 52, by forceps 55. The forceps 55 hold the IOL 37 in a specific and determinable planar orientation. Superior haptic 38 is placed forward of optic 37A, while the other haptic 38A trails the optic, as shown in FIG. 6. Hinged folding leaves 14 and 15 are moved together, which folds the flexible or foldable optic 37A of IOL 37 in half. After IOL 37 is folded, the forceps 55 is removed.

The closed loading cartridge 13, containing the folded IOL 37, is then loaded into body 21 of insertion apparatus 10, as described above.

Insertion apparatus 10 is operated and functions as follows. When it is desired to insert IOL 37 into an eye, the apparatus 10 and IOL 37 are placed in a configuration as shown in FIG. 3.

Figure 7:
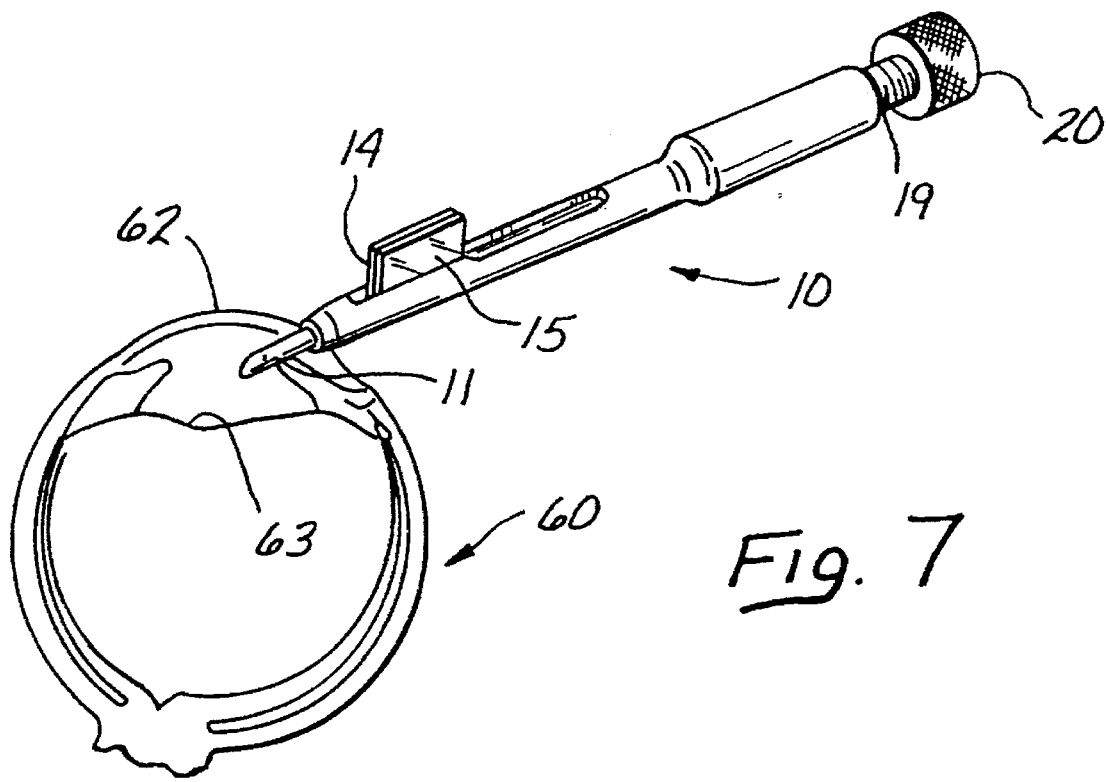
FIG. 7 is a schematic perspective drawing showing the placement of the distal portion of the insertion tube in the eye.

Referring now to FIG. 7, the IOL 37 is to be placed in eye 60 into an area formerly occupied by the natural lens of the eye. With the IOL 37 in its folded position within apparatus 10, forward tube 11 is ready for insertion through an incision 61 in the sclera 62 of eye 60. Capsular bag 63 protects the posterior segment of the eye 60, and is one of the eye's constituent parts which is not injured by the insertion of the IOL 37. With the forward tube 11 inserted within the eye 60 and the ejection port 12 positioned so that the IOL 37 can unfold in the location within the eye 60 best suited for permanent implantation, the operator advances plunger 19 by rotating cap 20. This action advances injector rod 33 distally, which in turn moves IOL 37 distally into the forward tube 11. Prior to the IOL 37 reaching the forward tube 11, cam follower 39 has engaged the distal end portion 40 of cam race 35. This prevents injector rod 33 from rotating as it advances IOL 37 from its initial position within folding cartridge 13.

As injector rod 33 advances farther distally, cam follower 39 engages the curved portion of cam race 35. This, in turn, causes injector rod 33 and IOL 37 to rotate. Cam race 35 illustrated in FIG. 3 allows injector rod 33 and IOL 37 to be rotated a maximum of 180 degrees from their original orientation. However, the extents of rotation can be any amount desired. Equally suitable extents of rotation can range from about 40 degrees or less to about 270 degrees or more, preferably about 90 degrees to about 180 degrees, in either direction from the IOL's original position. The degree of rotation can be chosen to permit the surgeon to hold insertion apparatus 10 in a position most convenient to the surgeon, while at the same time having the apparatus rotate the IOL a predetermined amount to assure its emergence from ejection port 12 in an orientation as close as possible to the IOL's final implanted position with reduced risk of damage to the eye.

FIG. 7 shows the sclera 62 having an incision through which the distal end portion of forward tube 11 is passed. Alternately, the incision can be made through the cornea. Forward tube 11 has a sufficiently small cross-section to pass into the eye 60 through a 3.0 mm incision in the sclera 62. Folding leaves 14 and 15, in contact with each other when lens folding cartridge 13 is in a closed position, can be grasped by an operator and used to guide and position insertion tube 11 in its desired position within the eye.

After IOL 37 has been inserted into eye 60, forward tube 11 is removed from eye 60. If needed, IOL 37 can be repositioned in the eye by a small, bent needle or similar tool inserted into the same incision.

Once IOL 37 is properly positioned in eye 60 and apparatus 10 is withdrawn from the eye, the incision in the sclera may be closed, for example, using conventional techniques.

After use, folding cartridge 13 is preferably disposed of. Remaining portions of apparatus 10 can be reused after sterilization and disinfection.

The present IOL insertion apparatus and methods effectively and straightforwardly control the orientation of the IOL as it is being inserted in the eye. This IOL orientation control is achieved without undue reliance on the technique and/or dexterity of the surgeon. Controlling the orientation of the IOL as it is being inserted reduces the risk of damaging components of the eye, and facilitates positioning the IOL in the eye in the desired location.

While this invention has been described with respect to various specific examples and embodiments, it is to be understood that the invention is not limited thereto and that it can be variously practiced within the scope of the following claims.

What is claimed is:

1. An apparatus for inserting a folded intraocular lens through an incision into an eye comprising:

a tube defining a hollow passage, said tube having an ejection opening through which said intraocular lens is passed from said hollow passage into an eye;

an injector rod longitudinally movable within said hollow passage of said tube, said injector rod having a distal portion adapted to contact the folded intraocular lens within said hollow passage of said tube to urge the folded intraocular lens distally through said hollow passage; and a rotation assembly located relative to said injector rod so that said distal portion of said injector rod is axially rotated a controlled amount as said injector rod is moved distally through said tube.

2. The apparatus of claim 1 wherein said rotation assembly comprises a cam race and a cam follower.

3. The apparatus of claim 2 wherein said cam race has a distal portion positioned substantially parallel to the longitudinal axis of said injector rod.

4. The apparatus of claim 2 wherein said cam race is disposed on said injector rod and said cam follower is disposed on said tube.

5. The apparatus of claim 1 wherein the amount of axial rotation of said distal portion of said injector rod by said rotation assembly is such that an intraocular lens present within said hollow passage is rotated in a range of about 40 degrees to about 270 degrees from an initial position within said hollow passage.

6. The apparatus of claim 1 wherein the amount of axial rotation of said distal portion of said injector rod by said rotation device is such that an intraocular lens present within said hollow passage is rotated axially in a range of about 90 degrees to about 180 degrees from an initial position within said hollow passage.

7. The apparatus of claim 1 wherein said tube is sized to pass said intraocular lens into the eye through an incision no larger than about 3.0 mm.

8. The apparatus of claim 1 wherein said injector rod is structured to engage the folded intraocular lens being moved distally through said tube.

9. The apparatus of claim 1 wherein said distal end portion of said injector rod includes a forceps-like element adapted to engage the folded intraocular lens being moved distally through said tube.

10. The apparatus of claim 9 wherein said forceps-like element includes at least two spaced apart members which are substantially stationary relative to each other.

11. The apparatus of claim 1 wherein said tube includes a cartridge adapted to fold the intraocular lens.

12. An apparatus for inserting a folded intraocular lens through an incision into an eye comprising:
   a tube defining a hollow passage, said tube having an ejection opening through which said intraocular lens is passed from said hollow passage into an eye;
   an injector rod longitudinally movable within said passage of said tube, said injector rod having a distal end portion which includes a forceps-like element including two spaced apart members which are substantially stationary relative to each other and are structured to engage the folded intraocular lens within said hollow passage of said tube; and
   a cam race disposed on said injector rod and a cam follower disposed on said tube, said cam race and said cam follower being positioned so that said distal end portion of said injector rod is axially rotated a controlled amount as said injector rod is moved distally through said tube.

13. A method for inserting an intraocular lens into an eye comprising:
   placing an intraocular lens in a folded condition in an insertion apparatus comprising a tube defining a hollow passage having an ejection opening through which said lens is ejected from said hollow space;
   an injector rod longitudinally movable within said hollow passage of said tube, said injector rod having a distal end portion adapted to contact the folded intraocular lens within said hollow passage to urge the folded intraocular lens distally through said hollow passage;
   a rotation assembly located relative to said injector rod so that said distal end portion of said injector rod is axially rotated a controlled amount as said injector rod is moved distally through said tube;
   positioning said ejection opening in proximity to or through an incision in said eye; and
   moving said injector rod distally.

14. The method of claim 13 wherein said tube is not rotated during said moving step.

15. The method of claim 13 wherein said intraocular lens is axially rotated by an amount substantially equal to the amount of axial rotation of said distal end portion of said injector rod.

16. A method according to claim 13 wherein said intraocular lens is axially rotated in a range of about 40 degrees to about 270 degrees from an initial orientation within said hollow passage.

17. A method according to claim 13 wherein said intraocular lens is axially rotated in a range of about 90 degrees to about 180 degrees from an initial orientation within said hollow passage.

18. The method of claim 13 wherein said distal end portion of said injector rod is structured to engage the folded intraocular lens being moved distally through said tube.

19. The method of claim 13 wherein said incision is no larger than about 3.0 mm.

* * * * *